(12) United States Patent
Schulz et al.

(10) Patent No.: US 8,894,666 B2
(45) Date of Patent: Nov. 25, 2014

(54) SURGICAL INSTRUMENT FOR APPLYING LIGATING CLIPS

(75) Inventors: Peter Schulz, Loeffingen (DE); Pedro Morales, Tuttlingen (DE); Dieter Weisshaupt, Immendingen (DE)

(73) Assignee: Aesculap AG, Tuttlingen (DE)

( * ) Notice: Subject to any disclaimer, the term of this patent is extended or adjusted under 35 U.S.C. 154(b) by 803 days.

(21) Appl. No.: 12/660,523

(22) Filed: Feb. 25, 2010

(65) Prior Publication Data

US 2010/0274262 A1    Oct. 28, 2010

(30) Foreign Application Priority Data

Apr. 24, 2009    (DE) .......................... 10 2009 018 821

(51) Int. Cl.
*A61B 17/128* (2006.01)
*A61B 17/29* (2006.01)

(52) U.S. Cl.
CPC ..... *A61B 17/1285* (2013.01); *A61B 2017/2911* (2013.01)
USPC ............ 606/143; 606/139; 606/142; 606/151

(58) Field of Classification Search
USPC ............... 227/175.1; 606/139, 142–143, 151, 606/157–158
See application file for complete search history.

(56) References Cited

U.S. PATENT DOCUMENTS

| | | | |
|---|---|---|---|
| 2,758,302 A | 8/1956 | White | |
| 3,378,010 A * | 4/1968 | Codling et al. | ............... 606/157 |
| 3,777,538 A | 12/1973 | Weatherly et al. | |
| 3,856,016 A | 12/1974 | Davis | |
| 3,954,108 A | 5/1976 | Davis | |
| 4,217,902 A * | 8/1980 | March | ........................... 606/221 |
| 4,299,224 A | 11/1981 | Noiles | |
| 4,412,539 A | 11/1983 | Jarvik | |
| 4,424,810 A * | 1/1984 | Jewusiak | ...................... 606/142 |
| 4,430,997 A | 2/1984 | DiGiovanni et al. | |

(Continued)

FOREIGN PATENT DOCUMENTS

| | | |
|---|---|---|
| CZ | 695 25 083 | 8/2002 |
| DE | 24 05 390 | 8/1975 |

(Continued)

OTHER PUBLICATIONS

Leaflet of Aesculap AG & Co. KG "Titanium Ligature Clips and Applicators", 8 pages, Feb. 2002.

(Continued)

*Primary Examiner* — Mark Mashack
(74) *Attorney, Agent, or Firm* — Lipsitz & McAllister, LLC (57) ABSTRACT

In a surgical instrument for applying C-shaped ligating clips having two juxtaposed legs which are joined to each other by a bridge portion and are each divided by a longitudinal slot into two juxtaposed portions joined to each other at the free end of the legs, the surgical instrument comprising two juxtaposed clamping jaws with guiding surfaces facing each other for the legs of a ligating clip that lie against the guiding surfaces when the ligating clip is inserted between the clamping jaws, in order to improve the positioning of the ligating clip between the clamping jaws, it is proposed that there be arranged on at least one of the guiding surfaces of the clamping jaws an inwardly protruding projection which, when the ligating clip is advanced along the guiding surfaces, elastically enters the longitudinal slot of the ligating clip.

13 Claims, 7 Drawing Sheets

(56) References Cited

U.S. PATENT DOCUMENTS

| | | | |
|---|---|---|---|
| 4,478,220 A | 10/1984 | Di Giovanni et al. | |
| 4,509,518 A | 4/1985 | McGarry et al. | |
| 4,512,345 A | 4/1985 | Green | |
| 4,799,481 A * | 1/1989 | Transue et al. | 606/158 |
| 4,854,317 A | 8/1989 | Braun | |
| 4,979,950 A * | 12/1990 | Transue et al. | 606/158 |
| 4,983,176 A | 1/1991 | Cushman et al. | |
| 5,047,038 A | 9/1991 | Peters et al. | |
| 5,160,339 A | 11/1992 | Chen et al. | |
| 5,171,250 A | 12/1992 | Yoon | |
| 5,207,692 A * | 5/1993 | Kraus et al. | 606/143 |
| 5,217,473 A | 6/1993 | Yoon | |
| 5,366,459 A | 11/1994 | Yoon | |
| 5,441,509 A | 8/1995 | Vidal et al. | |
| 5,527,320 A | 6/1996 | Carruthers et al. | |
| D371,390 S | 7/1996 | Johnson | |
| 5,609,599 A | 3/1997 | Levin | |
| 5,626,585 A | 5/1997 | Mittelstadt et al. | |
| 5,665,097 A | 9/1997 | Baker et al. | |
| 5,681,330 A | 10/1997 | Hughett et al. | |
| 5,700,271 A | 12/1997 | Whitfield et al. | |
| 5,725,542 A | 3/1998 | Yoon | |
| 5,772,673 A | 6/1998 | Cuny et al. | |
| 5,779,720 A | 7/1998 | Walder-Utz et al. | |
| 5,788,716 A | 8/1998 | Kobren et al. | |
| D401,626 S | 11/1998 | Shyu | |
| 5,843,097 A | 12/1998 | Mayenberger et al. | |
| 6,015,417 A | 1/2000 | Reynolds, Jr. | |
| 6,352,541 B1 * | 3/2002 | Kienzle et al. | 606/143 |
| 6,428,548 B1 | 8/2002 | Durgin et al. | |
| 6,837,895 B2 | 1/2005 | Mayenberger | |
| 7,207,997 B2 | 4/2007 | Shipp et al. | |
| 7,572,266 B2 | 8/2009 | Young et al. | |
| D600,749 S | 9/2009 | Azman et al. | |
| D600,750 S | 9/2009 | Azman et al. | |
| 7,648,514 B1 * | 1/2010 | Nakao | 606/142 |
| 7,678,125 B2 | 3/2010 | Shipp | |
| 8,585,718 B2 * | 11/2013 | Disch et al. | 606/143 |
| 2002/0099388 A1 | 7/2002 | Mayenberger | |
| 2004/0147942 A1 | 7/2004 | Chao | |
| 2005/0177177 A1 | 8/2005 | Viola | |
| 2006/0212049 A1 | 9/2006 | Mohiuddin | |
| 2008/0045981 A1 | 2/2008 | Margolin et al. | |
| 2008/0312670 A1 | 12/2008 | Lutze et al. | |
| 2012/0048759 A1 * | 3/2012 | Disch et al. | 206/339 |

FOREIGN PATENT DOCUMENTS

| | | |
|---|---|---|
| DE | 30 21 099 | 12/1980 |
| DE | 37 04 760 | 3/1988 |
| DE | 44 29 084 | 6/1995 |
| DE | 690 28 200 | 2/1997 |
| DE | 691 22 002 | 2/1997 |
| DE | 196 03 889 | 8/1997 |
| DE | 696 34 391 | 1/2006 |
| DE | 20 2006 000 329 | 3/2006 |
| DE | 20 2006 011 054 | 9/2006 |
| DE | 10 2006 001 344 | 7/2007 |
| DE | 20 2007 003 398 | 7/2007 |
| DE | 696 36 965 | 12/2007 |
| EP | 0 567 965 | 11/1993 |
| EP | 0 697 198 | 2/1996 |
| EP | 1 198 204 | 4/2002 |
| WO | 96/32891 | 10/1996 |
| WO | 98/18389 | 5/1998 |
| WO | 99/27859 | 6/1999 |

OTHER PUBLICATIONS

Brochure of Aesculap AG & Co. KG "Challenger Ti", 12 pages, Feb. 2002.

* cited by examiner

FIG.6 ary SURGICAL INSTRUMENT FOR APPLYING
LIGATING CLIPS

The present disclosure relates to the subject matter disclosed in German application number 10 2009 018 821.5 of Apr. 24, 2009, which is incorporated herein by reference in its entirety and for all purposes.

BACKGROUND OF THE INVENTION

The invention relates to a surgical instrument for applying C-shaped ligating clips having two juxtaposed legs which are joined to each other by a bridge portion and are each divided by a longitudinal slot into two juxtaposed portions joined to each other at the free end of the legs, the surgical instrument comprising two juxtaposed clamping jaws with guiding surfaces facing each other for the legs of a ligating clip that lie against the guiding surfaces when the ligating clip is inserted between the clamping jaws.

In such surgical instruments, ligating clips are mostly advanced in the distal direction out of a cartridge arranged in a shaft in which they lie in a row one behind the other, and the respective foremost ligating clip is pushed out of the cartridge in between the clamping jaws until the ligating clip is in a foremost applying position. In this position, the ligating clip can be applied to a vessel or some other piece of tissue and then closed by the two clamping jaws being brought close together. The legs of the ligating clip are thereby bent towards each other.

It is important for the ligating clips to maintain their position between the clamping jaws during the applying and closing procedure. For this reason, it is known to provide retaining projections on the cartridge, which fix the ligating clips in the advanced applying position. Such fixing is, however, not possible if the applying position is located at a large spacing from the cartridge.

The object of the invention is to so construct a generic surgical instrument that specifically for ligating clips which are divided into two portions and have a longitudinal slot, a secure positioning of the ligating clip in the foremost applying position is achievable.

SUMMARY OF THE INVENTION

This object is accomplished in accordance with the invention in a surgical instrument of the kind described at the outset in that there is arranged on at least one of the guiding surfaces of the clamping jaws an inwardly protruding projection which, when the ligating clip is advanced along the guiding surfaces, elastically enters the longitudinal slot of the ligating clip.

Accordingly, specifically in the case of ligating clips having a longitudinal slot, this longitudinal slot is utilized to allow a projection to enter this longitudinal slot, more particularly, elastically, so that the ligating clip can be pushed past this projection before the projection enters the longitudinal slot.

Once the projection enters the longitudinal slot, the ligating clip can no longer be pushed back past the projection as the two portions of the leg of the ligating clip are joined to each other at the free end of the leg and therefore close the longitudinal slot at this point.

It is particularly advantageous for the projection, upon entering the longitudinal slot, to come into abutment against the two juxtaposed portions of the leg. Thus, the projection not only acts to prevent the ligating clip from being unintentionally pushed back, but, at the same time, this projection also assumes the task of guiding the ligating clip.

This action is further reinforced if, in accordance with a preferred embodiment, the projection, upon entering the longitudinal slot, comes into abutment, in the longitudinal direction of the longitudinal slot, with various points and/or over a continuous area with the two juxtaposed portions of the leg. In this case, the ligating clip is no longer able to move out of the plane defined by the longitudinal slots, as the projection or projections enter the longitudinal slot and prevent any pivotal movement of the ligating clip out of this plane. Such guidance is particularly advantageous if the ligating clip, when being advanced in the clamping jaws, is not guided over the entire length of the legs but, for example, only in the area of the free ends, as is the case with legs which diverge from the bridge portion to the free end.

In a first embodiment, it may be provided that the projection is elastically displaceable against that clamping jaw on which it is mounted. Therefore, when the ligating clip is being advanced, the projection is pushed elastically against the clamping jaw, so that the free end of the legs at which the two portions of the leg are joined to each other can be pushed past the projection that has been moved elastically out of the path of advancement of the ligating clip. Once the free end is pushed past the projection, the projection moves again elastically inwards and enters the longitudinal slot of the ligating clip, so that the latter is guided and secured against unintended rearward movement.

The projection may, for example, be constructed as a resilient tongue.

It is, however, also possible for the projection to be of permanently projecting construction, and for the legs of the ligating clip to be adapted to move elastically relative to each other. In this case, the ligating clip can be moved past the fixed projection by the legs being bent together elastically to a slight extent. Once the free ends of the legs have been pushed past the projection, the legs open out again, so that the projection then enters the longitudinal slot.

The projection may be integrally formed on the clamping jaws, but it is also possible for the projection to be a separate component which is joined to the clamping jaw.

For example, the projection may be a metallic strip which extends along the longitudinal slot and, for example, is embedded in the plastic material of a clamping jaw.

It is particularly advantageous for the projection to have at its distal end an end surface extending transversely to the direction of advance of the ligating clip. After the ligating clip has slid past, the end surface positions itself on the rear side of the ligating clip and safely prevents any moving back of the ligating clip.

It is expedient for the depth of entry of the projection into the longitudinal slot of the ligating clip to be maximally as large as the material thickness of the legs in the area of entry of the projection. As a result, the projection does not protrude inwardly beyond the legs of the ligating clip, so that when the ligating clip is applied to a vessel, this vessel comes into contact with the legs of the ligating clip only and not with the projection entering the longitudinal slot of the ligating clip.

The instrument can be used with particular advantage in the case of a ligating clip in which the legs of the ligating clip diverge from the bridge portion to the free ends of the legs, so that the legs abut only at their free ends against the clamping jaws. Such a ligating clip configuration has the advantage, firstly, that the surgeon has a larger opening cross section at his disposal when applying the ligating clip, and, secondly, the ligating clips placed in a row one behind the other in a cartridge of the instrument can thereby be positioned much closer to one another since an overlapping of consecutive ligating clips is thus possible in the area of their legs.

The following description of preferred embodiments of the invention serves in conjunction with the drawings to provide a detailed explanation.

DETAILED DESCRIPTION OF THE INVENTION

The surgical instrument 1 shown in the drawings comprises an elongate shaft 2 which at its proximal end opens into a handle part 3. Inserted in the shaft 2 is a cartridge 4 in which a fairly large number of ligating clips 5 are accommodated one behind the other. The ligating clips 5 are of overall C-shaped design with two juxtaposed legs 6, 7 which are joined to each other by a bridge portion 8. The ligating clips 5 consist of two portions 9, 10 extending in a juxtaposed manner over the entire length of the ligating clip, which are joined to each other only at the free ends 11, 12 of the legs 6, 7 and over the remaining length of the ligating clips 5 include a longitudinal slot 13 between them.

Figure 1:
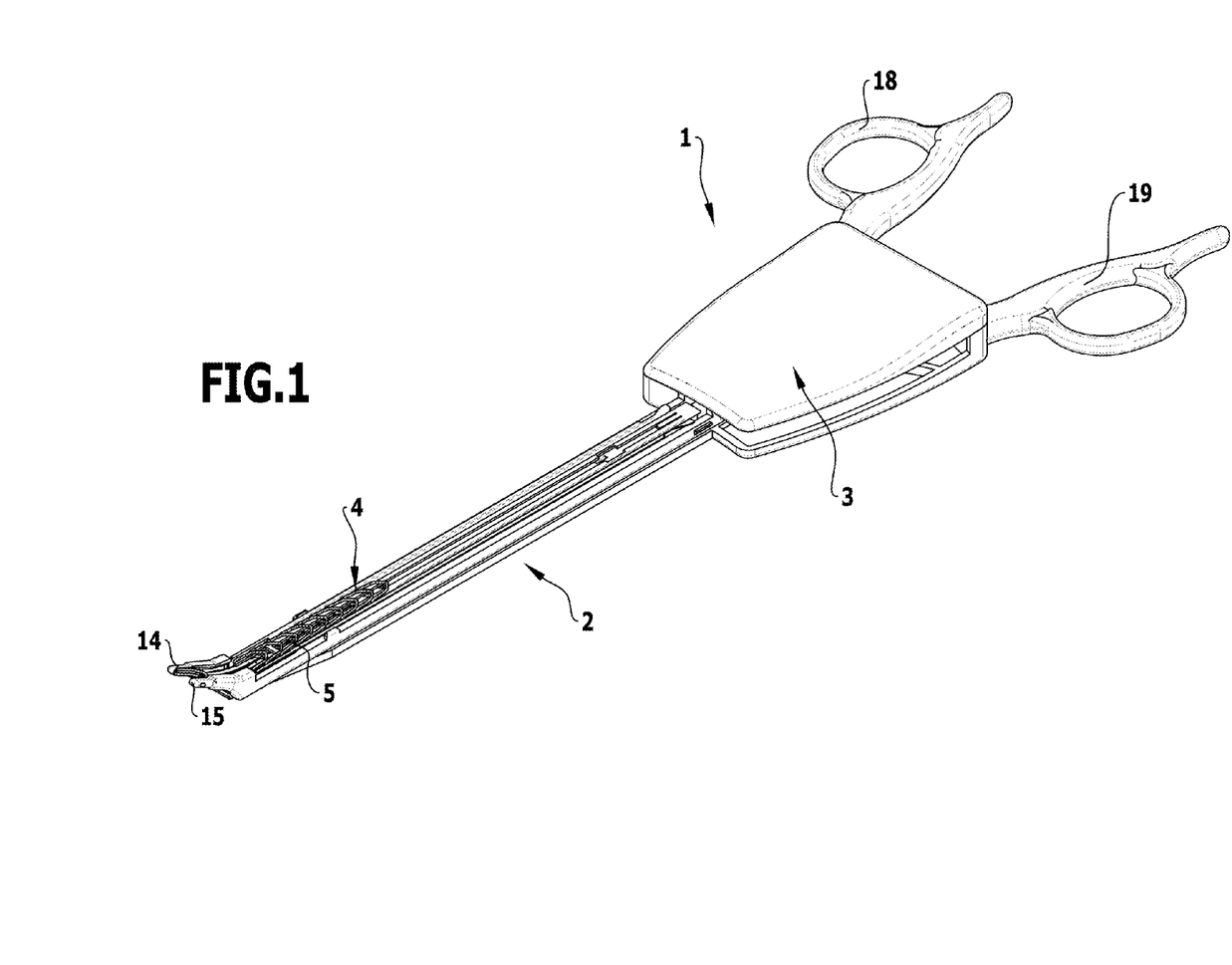
FIG. 1 shows a perspective view of an instrument for applying ligating clips.
Figure 2:
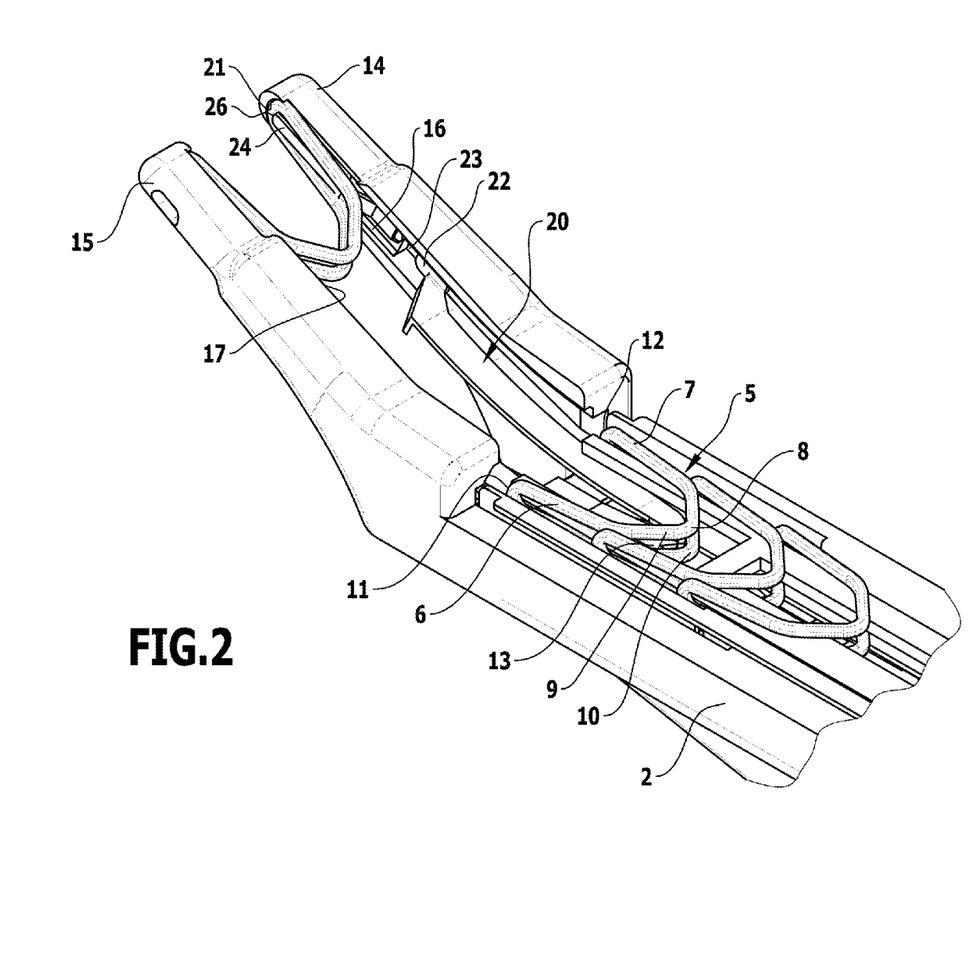
FIG. 2 shows a perspective detailed view of the clamping jaws and the adjacent cartridge area with the cover removed and with a ligating clip between the two clamping jaws.
Figure 3:
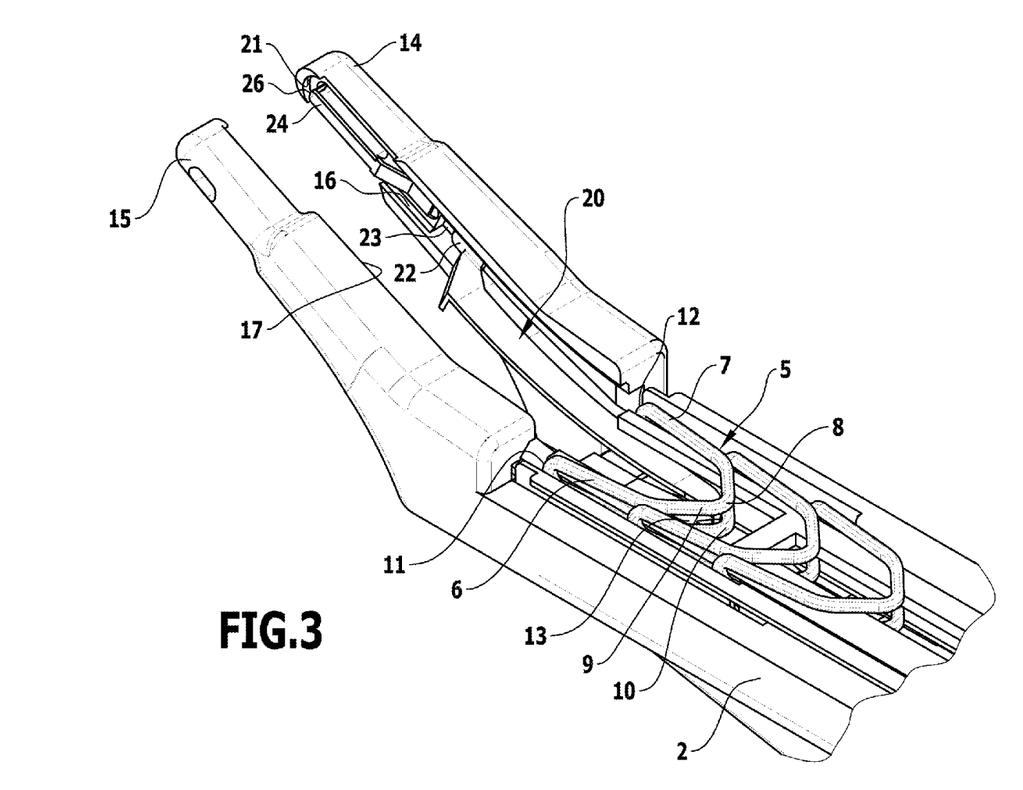
FIG. 3 shows a view similar to FIG. 2 without any ligating clip between the clamping jaws.

The ligating clips 5 are arranged in such a way in the cartridge 4 that the free ends 11, 12 point in the distal direction, and the legs 6, 7 are constructed so as to diverge slightly in the direction towards the free end, so that the free ends 11, 12 of a ligating clip can be positioned next to the proximal end of the legs 6, 7 of the ligating clip 5 that is arranged further in the distal direction in the cartridge 4, i.e., the legs 6, 7 of consecutive ligating clips can overlap slightly (FIGS. 2 and 3).

Arranged in a juxtaposed manner at the distal end of the shaft 2 are two clamping jaws 14, 15, which comprise guiding surfaces 16, 17 facing each other, which are formed, for example, by longitudinal grooves in the clamping jaws 14, 15 and which, when a ligating clip 5 is advanced, lie against the outer side of the legs 6, 7 and thereby guide the ligating clip 5. Since the legs 6, 7 of the ligating clip 5 diverge, the legs 6, 7 lie essentially only in the area of the free ends 11, 12 against the guiding surfaces 16, 17.

The guiding surfaces 16, 17 in the embodiment shown are bent in accordance with the inclination of the clamping jaws 14, 15 in relation to the plane in which the ligating clips 5 are arranged in the cartridge 4, and the spacing of the distal end of the cartridge 4 from the distal end of the guiding surface 16, 17 is significantly larger than the length of a ligating clip 5.

There are mounted on the handle part 3 two pivotable handle elements 18, 19, which can be pivoted relative to each other and thereby actuate an advancing device via gears known per se, not shown in the drawings, which are arranged in the handle part 3 and in the shaft 2. On the one hand, the ligating clips 5 arranged in the cartridge 4 are advanced stepwise by one position in the distal direction, in each case, by the advancing device. On the other hand, this advancing device also comprises a band-shaped advancing element 20 which advances the respective foremost ligating clip in the cartridge 4 from this position as far as an applying position between the clamping jaws 14, 15, in which the ligating clip 5 strikes a stop surface 21 at the distal end of the clamping jaws 14. For this purpose, the advancing element 20 is guided along the path of advance by guiding elements 22 at the side, which enter a longitudinal groove 23 in the clamping jaws. This advancing element 20 can be advanced and retracted by actuation of the handle elements 18, 19, so that with each advance a ligating clip 5 is pushed forwards out of the cartridge up to between the clamping jaws, whereas during retraction, the advancing element 20 withdraws to behind the foremost ligating clip in the cartridge and can then take it along during the next advance and push it in between the clamping jaws.

Inwardly protruding projections 24, 25 are provided on the guiding surfaces 16, 17 of the clamping jaws 14, 15. In the case of the embodiment of FIGS. 1 to 4, these projections 24, 25 are formed by a metallic tongue-shaped leaf spring, which is connected at its proximal end to the clamping jaw, for example, by being embedded in the plastic material of the clamping jaw, and whose free end is bent outwards at a right angle and forms there an end surface 26 which extends transversely to the direction of advance of the ligating clips 5. The projections 24, 25 are arranged at the center of the guiding surfaces 16, 17, and their width is slightly smaller than the width of the longitudinal slots 13 in the ligating clips 5.

When a ligating clip 5 is advanced in the distal direction, the free ends 11, 12 at which the two portions 9, 10 of the ligating clip 5 are joined to each other first slide past the projections 24, 25 and bend these elastically outwards, so that the free ends 11, 12 can slide past the projections 24, 25. Once this is the case, the elastic projections 24, 25 pivot on account of their elasticity back into their undeformed starting position in which they protrude inwards and thereby enter the longitudinal slot 13 between the portions 9, 10 of the ligating clip 5. They thereby come into abutment over a fairly large portion of the length of the legs against the two portions 9, 10, so that the ligating clip is secured in this position against pivoting out of the plane of the ligating clip. In addition, the end surfaces 26 position themselves on the free ends 11, 12 of the ligating clip 5, so that the ligating clip 5 can no longer be pushed back in the proximal direction. The projections 24, 25 thus assume a double function, namely, on the one hand, the securing of the ligating clip against unintended retraction, and, on the other hand, also a securing of the ligating clip against pivotal movement out of its own plane. This is of importance, particularly when the legs of the ligating clip—as in the embodiment shown—are of diverging construction and therefore abut only at the free end on the guiding surfaces 16, 17. By virtue of the projections 24, 25 entering the longitudinal slot 13, there is also provided, beyond this guidance in the area of the free ends 11, 12, a guidance for the ligating clips in the remaining leg area, so that the ligating clips are reliably secured in the applying position in which they abut at the free ends 11, 12 on the stop surface 21. In the embodiment shown in FIGS. 1 to 4, the spacing of the end surfaces 26 of the projections 24, 25 from the stop surface 21 is so selected that exactly those parts of the ligating clip which join the two portions 9, 10 to each other at the free ends 11, 12 fit into the space. The ligating clip is thereby secured against displacement both distally and proximally.

Figure 4:
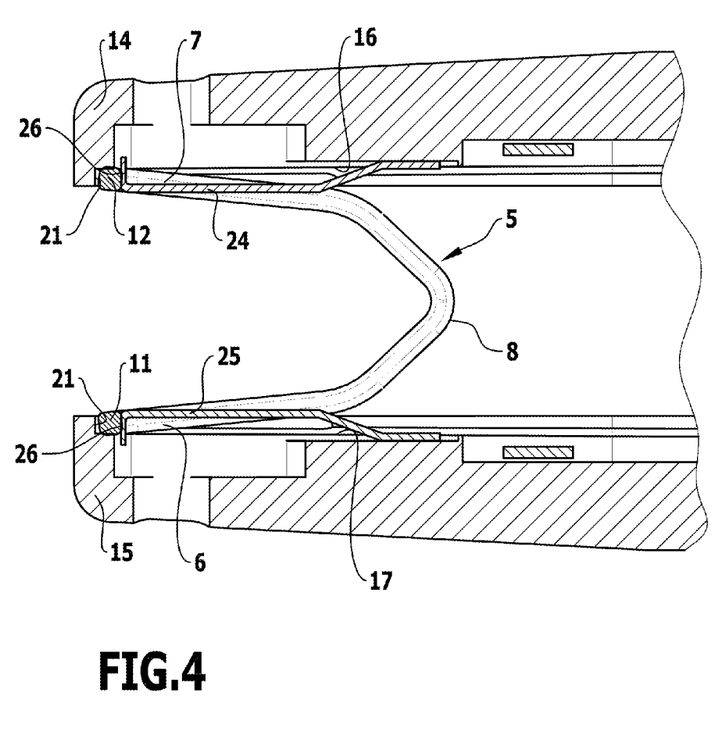
FIG. 4 shows a longitudinal sectional view of a preferred embodiment of two clamping jaws with a projection in the form of a metallic spring tongue.
Figure 5:
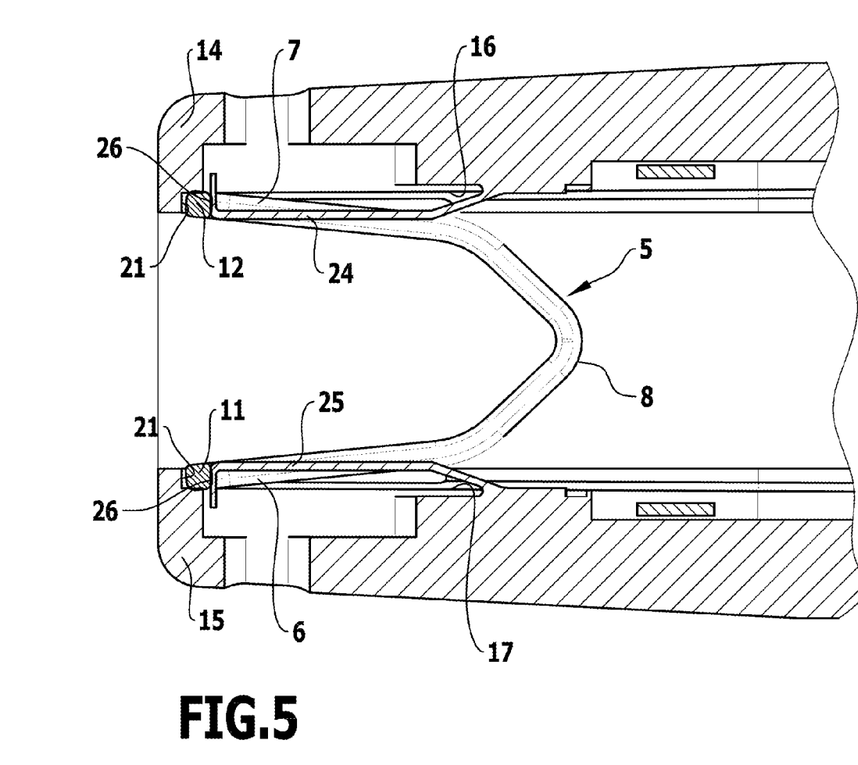
FIG. 5 shows a view similar to FIG. 4 with a projection in the form of a spring tongue formed integrally on the clamping jaws.

Whereas in the embodiment of FIG. 4 the projections 24, 25 are constructed as metallic spring tongues which are joined to the clamping jaws 14, 15, i.e., constitute independent components, in the embodiment of FIG. 5, which is otherwise of identical design and in which like parts are given like reference numerals, the projections 24, 25 are constructed integrally with the clamping jaws 14, 15, in the embodiment shown, however, in a similar manner, as spring tongues.

Figure 6:
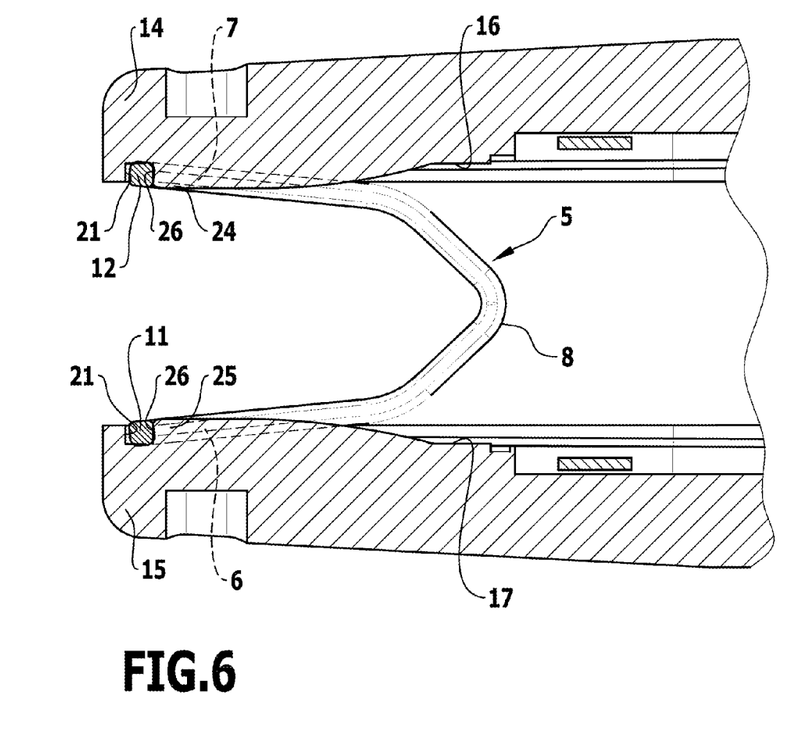
FIG. 6 shows a view similar to FIG. 5 with a permanent projection which is integrally formed on the clamping jaws and is unable to undergo elastic deformation.

In contrast thereto, in the embodiment of FIG. 6, which is otherwise of identical design and in which corresponding parts are given the same reference numerals, projections 24, 25 are selected, which are not of resilient construction, but protrude inwards as part of the clamping jaws 14, 15. When, in this embodiment, the ligating clips 5 are advanced, the legs 6, 7 spring inwards slightly when the free ends 11, 12 of the legs 6, 7 slide past the projections 24, 25 and then spring out again into a space between the end surface 26 of the projections 24, 25 and the stop surface 21 at the end of the guiding surfaces 16, 17. In this case, the inherent elasticity of the ligating clip is utilized in order to be able to push it past the projections.

In all cases, it is expedient for the depth of entry of the projections 24, 25 not to exceed the width or thickness of the legs 6, 7, i.e., for the projections 24, 25 not to protrude inwards beyond the legs 6, 7 when they engage the longitudinal slot 13.

Figure 4A:
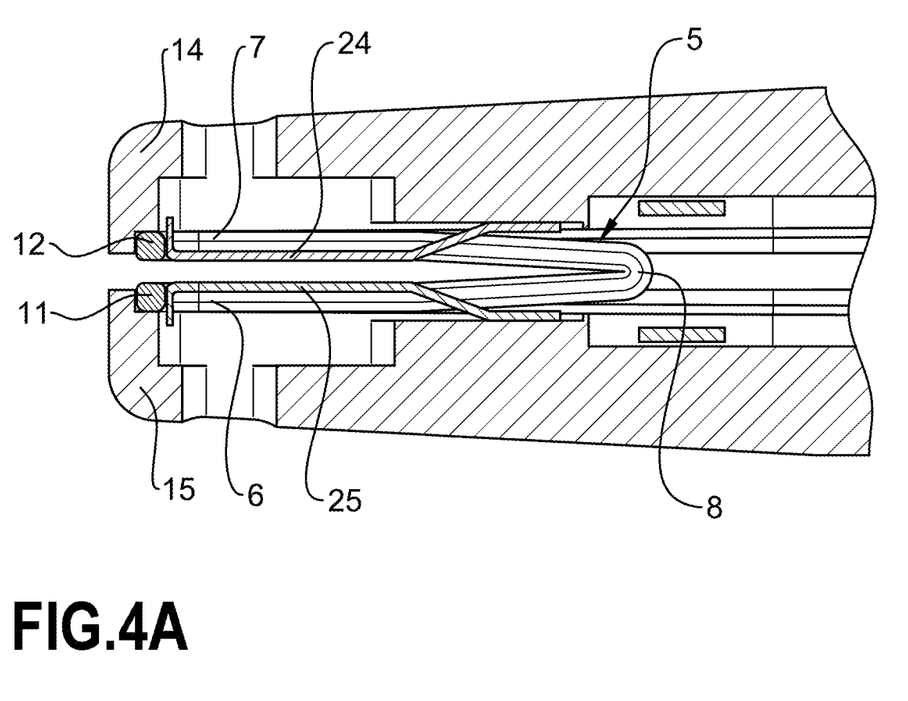
FIG. 4A shows the clamping jaws of the FIG. 4 embodiment in a closed or clamping position.

Since the projections 24, 25 are held on the clamping jaws 14, 15, these projections 24, 25 can also secure the ligating clip during the entire clamping procedure in this position in which the clamping jaws are moved towards each other and thereby advance the legs towards each other (e.g., as shown in FIG. 4A). It is thus ensured that during the entire applying procedure the ligating clip is secured in the applying position against displacement and against pivotal movement. Since the guidance of the ligating clips against pivotal movement is ensured by the projections 24, 25, it is not necessary for the clamping jaws to embrace the outer side of the legs in order to guide these, and, therefore, the clamping jaws can be of very slim construction, in particular, in the distal clamping jaw area and thereby allow the surgeon optimum visibility of the applying area.

The invention claimed is:

1. Surgical instrument for applying C-shaped ligating clips in combination with C-shaped ligating clips, comprising:
    a cartridge adapted to be inserted into said surgical instrument;
    a plurality of C-shaped ligating clips arranged in the cartridge, each of the C-shaped ligating clips comprising two juxtaposed legs which are joined to each other by a bridge portion, the legs defining an open distal end opposite the bridge portion, each of the ligating clips being divided by a longitudinal slot into two juxtaposed portions joined to each other at distal free ends of the legs, said surgical instrument comprising:
    two juxtaposed clamping jaws with respective guiding surfaces facing each other for the legs of one of the ligating clips that lies against the guiding surfaces when the ligating clip is inserted between the clamping jaws, the two juxtaposed clamping jaws being adapted to close the open distal end of the ligating clip by advancing the distal free ends of the legs towards each other; and
    an inwardly protruding projection arranged on at least one of the guiding surfaces of the clamping jaws which, when the ligating clip is advanced along the guiding surfaces, elastically enters the longitudinal slot of the ligating clip.

2. Surgical instrument in accordance with claim 1, wherein the projection, upon entering the longitudinal slot, comes into abutment against the two juxtaposed portions of the leg.

3. Surgical instrument in accordance with claim 2, wherein the projection, upon entering the longitudinal slot, comes into abutment, in a longitudinal direction of the longitudinal slot, with various points and/or over a continuous area with juxtaposed portions of the leg.

4. Surgical instrument in accordance with claim 2, wherein the projection is of permanently projecting construction, and the legs of the ligating clip are adapted for pivotal movement elastically relative to each other.

5. Surgical instrument in accordance with claim 1, wherein the projection is elastically displaceable against that clamping jaw on which it is mounted.

6. Surgical instrument in accordance with claim 5, wherein the projection is constructed as a resilient tongue.

7. Surgical instrument in accordance with claim 1, wherein the projection is of permanently projecting construction, and the legs of the ligating clip are adapted for pivotal movement elastically relative to each other.

8. Surgical instrument in accordance with claim 1, wherein the projection is integrally formed on the clamping jaws.

9. Surgical instrument in accordance with claim 1, wherein the projection is a separate component which is joined to the clamping jaw.

10. Surgical instrument in accordance with claim 9, wherein the projection is a metallic strip extending along the longitudinal slot.

11. Surgical instrument in accordance with claim 1, wherein the projection has at a distal end an end surface extending transversely to a direction of advance of the ligating clip.

12. Surgical instrument in accordance with claim 1, wherein a depth of entry of the projection into the longitudinal slot of the ligating clip is maximally as large as a material thickness of the legs in an area of entry of the projection.

13. Surgical instrument in accordance with claim 1, wherein the legs of the ligating clip diverge from the bridge portion to the free ends of the legs, so that the legs abut only at the free ends against the guiding surfaces of the clamping jaws.

* * * * *